(12) United States Patent
Stanford et al.

(10) Patent No.: US 6,432,714 B2
(45) Date of Patent: *Aug. 13, 2002

(54) PROPHYLACTIC AND THERAPEUTIC METHOD

(75) Inventors: John Lawson Stanford, Marden; Graham A. W. Rook, Haverhill, both of (GB)

(73) Assignee: Stanford Rook Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/793,713

(22) Filed: Feb. 27, 2001

Related U.S. Application Data

(63) Continuation-in-part of application No. 08/442,298, filed on May 16, 1995, now Pat. No. 6,210,684, which is a continuation of application No. 08/312,673, filed on Sep. 28, 1994, now abandoned, which is a continuation of application No. 08/031,307, filed on Mar. 15, 1993, now abandoned, which is a continuation-in-part of application No. 07/820,684, filed on Mar. 27, 1992, now abandoned.

(51) Int. Cl.⁷ .......................... C12N 1/20; C12N 5/06; C12Q 1/70; C12Q 1/06
(52) U.S. Cl. .......................... 435/863; 435/5; 435/39; 435/339.1
(58) Field of Search .......................... 435/5, 39, 339.1, 435/863

(56) References Cited

U.S. PATENT DOCUMENTS 6,001,361 A * 12/1999 Tan et al. ................ 424/190.1

* cited by examiner

Primary Examiner—Hankyel T. Park
(74) Attorney, Agent, or Firm—Pillsbury Winthrop LLP

(57) ABSTRACT

Antigenic and/or immunoregulatory material derived from *Mycobacterium vaccae* is useful in the prophylaxis or therapy of AIDS with or without associated tuberculosis.

8 Claims, No Drawings

PROPHYLACTIC AND THERAPEUTIC METHOD

This application is a continuation-in-part application of U.S. Ser. No. 08/442,298, filed May 16, 1995, now U.S. Pat. No. 6,210,684 which is a continuation of Ser. No.08/312,673, filed Sep. 28, 1994, abandoned which is a continuation of Ser. No. 08/031,307, filed Mar. 15, 1993, abandoned which is a continuation-in-part of Ser. No. 07/820,684 filed Mar. 27, 1992 abandoned, which claims priority to PCT GB90/01169, filed Jul. 27, 1990, GB 8917256.3, filed Jul. 28, 1989, and GB 9219425.7, filed Sep. 14, 1992, all of which are incorporated herein by reference.

BACKGROUND OF THE INVENTION

1. Field of the Invention

This invention relates to the prophylaxis and therapy of AIDS (acquired immune deficiency syndrome).

2. Background Information

The causative agent for AIDS is known to be a virus of the retrovirus family called HIV (human immunodeficiency virus). Infection with HIV does not, however, immediately give rise to overt symptoms of AIDS. The only indication of exposure to the virus may be the presence of antibodies thereto in the blood of an infected subject who is then described as "HIV positive." The infection may lie dormant, giving rise to no obvious symptoms, and the incubation period prior to development of AIDS may vary from several months to several decades.

The reasons for the variable period between infection with the virus and breakdown of the immune system in an infected individual is poorly understood. Factors at present unknown may trigger proliferation of the virus with consequential disruption of the immune system. The victims of the disease are then subject to various infections and malignancies which, unchecked by the disabled immune system, lead to death.

Infection with HIV can, over time, weaken the immune system to the point where the infected individual has difficulty fighting off certain infections that are usually controlled by a healthy immune system. These infections are known as "opportunistic" infections because they take the opportunity to infect individuals with weakened immune systems.

An HIV infected person receives a diagnosis of AIDS after developing one of the AIDS indicator illnesses as defined by the U.S. Centers for Disease Control. These conditions include Candidiasis of bronchi, trachea, or lungs
Candidiasis, esophageal
Cervical cancer, invasive
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminiated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
Mycobacterium avium complex or M. kansasii, disseminated or extrapulmonary
Mycobacterium tuberculosis, any site (pulmonary or extrapulmonary)
Mycobacterium, other species or unidentified species, disseminated or extrapulmonary
Pneumocystis carinii pneumonia
Pneumonia, recurrent
Progressive multifocal leukoencephalopathy
Salmonella septicemia, recurrent
Toxoplasmosis of brain
Wasting syndrome due to HIV An HIV positive person who has not had any serious illnesses can also receive an AIDS diagnosis on the basis of certain blood tests, in particular a CD4+ count.

Despite rapid growth of research into AIDS, no effective vaccine against it is yet available: it has been suggested that the genetic variability of the virus will in fact hamper the search for an effective vaccine.

The association between HIV infection and tuberculosis is well known. An early effect of HIV infection is the reactivation of previously dormant tubercule bacilli. The maintenance of resistance to mycobacteria is an active immunological process which is compromised by HIV infection. In dually infected persons, there is a high reactivation rate of dormant tubercule bacilli, and this reactivation usually occurs well before the appearance of other HIV/AIDS-related infections, which strongly suggests that an important effect of HIV infection is to destroy precisely those immune functions, presumably T-cell mediated, that maintain mycobacterial dormancy.

There is also evidence that where active tuberculosis is superimposed on HIV infection, there is a dramatic loss of CD4 T-cells which results in very rapid development of overt symptoms of AIDS. It appears in fact that immune mediators released in tuberculosis accelerate transactivation of the HIV provirus.

We have previously described the use of antigenic and/or immunoregulatory material derived from *Mycobacterium vaccae* in the treatment of tuberculosis (see, for example, British Patent No. 2,156,673 and U.S. Pat. No. 4,724,144).

SUMMARY OF THE INVENTION

We have now discovered that the same therapeutic agent not only delays development of AIDS in patients infected by HIV, but also is capable of causing regression, or even removal, of overt symptoms of AIDS even in patients where the disease is far advanced. These effects have been found in patients suffering also from tuberculosis, but are expected to occur also in patients who are suffering from HIV infection with or without AIDS and without associated tuberculosis.

The present invention accordingly provides a method for the prophylaxis or therapy of AIDS comprising administering to a subject who has been exposed to HIV infection or is HIV positive with or without overt symptoms of AIDS, killed cells of *Mycobacterium vaccae* in an amount sufficient to provoke an immune response effective to delay or prevent onset, or reduce the severity, of AIDS. The subject may or may not also show overt symptoms of tuberculosis.

The present invention also provides a method for reducing viral load in an HIV positive subject with or without AIDS.

This object is achieved by administering to the subject killed cells of Mycobacterium vaccae in an amount effective to reduce HIV viral load.

The invention furthermore provides a method for stimulating an immune response in an HIV positive subject with or without AIDS. This object is achieved by administering to the subject killed cells of Mycobacterium vaccae in an amount effective to stimulate an immune response in said subject.

Means for achieving these and other objectives of the invention are set forth in the examples below, which are intended to describe the invention but not to limit it.

DETAILED DESCRIPTION OF THE INVENTION

Therapeutic agents which may be used in the present invention comprise dead cells of M. vaccae, preferably cells which have been killed by autoclaving. The immunotherapeutic agent normally comprises more than $10^8$ microorganisms per ml of diluent, and preferably from $10^8$ to $10^{11}$ killed M. vaccae microorganisms per ml of diluent.

The diluent may be pyrogen-free saline for injection alone, or a borate buffer of pH 8.0. The diluent should be sterile. A suitable borate buffer is:

| | |
|---|---|
| $Na_2B_4O_7 \cdot 10H_2O$ | 3.63 g |
| $H_3BO_3$ | 5.25 g |
| NaCl | 6.19 g |
| Tween | 0.0005% |
| Distilled water | to 1 liter |

The preferred strain of M. vaccae is one denoted R877R isolated from mud samples from the Lango district of Central Uganda (J. L. Stanford and R. C. Paul, Ann. Soc. Belge Med, Trop. 1973, 53, 389). The strain is a stable rough variant and belongs to the aurum sub-species. It can be identified as belonging to M. vaccae by biochemical and antigenic criteria (R. Bonicke, S. E. Juhasz., Zentr albl. Bakteriol. Parasitenkd. Infection skr. Hyg. Abt. 1, Orig., 1964, 192, 133).

The strain denoted R877R has been deposited at the National Collection of Type Cultures (NCTC) Central Public Health Laboratory, Colindale Avenue, London NW9 5HT, United Kingdom on Feb. 13, 1984 under the number NCTC 11659.

For the preparation of an immunotherapeutic agent which may be used in the method of the present invention, the microorganism M. vaccae may be grown on a suitable solid medium. A modified Sauton's liquid medium is preferred (S. V. Boyden and E. Sorkin, J. Immunol, 1955, 75, 15) solidified with agar.

Preferably the solid medium contains 1.3% agar. The medium inoculated with the microorganisms is incubated aerobically to enable growth of the microorganisms to take place, generally at 32° C. for 10 days. The organisms are harvested, then weighed and suspended in a diluent. The diluent may be unbuffered saline but is preferably borate-buffered and contains a surfactant such as Tween 80 as described above. The suspension is diluted to give 100 mg of microorganism/ml. For further dilution, borate-buffered saline is preferably used so that the suspension contains 10 mg wet weight of microorganisms/ml of diluent. The suspension may then be dispensed into 5 ml multidose vials. Although the microorganisms in the vials may be killed using irradiation, e.g., from $^{60}$Cobalt at a dose of 2.5 megarads, or by any other means, for example, chemically, it is preferred to kill the microorganisms by autoclaving, for example, at 10 psi for 10 minutes (115°–125°). It has been discovered that autoclaving yields a more effective preparation than irradiation.

The immunotherapeutic agent is in general administered by injection in a volume in the range of 0.1–0.2 ml, preferably 0.1 ml, given intradermally. A single dosage will generally contain from $10^7$ to $10^{10}$ killed M. vaccae microorganisms. It is preferred to administer to patients a single dose containing $10^8$ to $10^9$ killed M. vaccae. However, the dose may be repeated depending on the condition of the patient.

Although the immunotherapeutic agent will generally be administered by intradermal injection, other routes, e.g., oral administration, can also be used.

For 20 to 50% of African patients with HIV infection, tuberculosis is the first symptom in development of AIDS. Tuberculosis infection is associated with significant production of interleukin 6 (IL6) and tumour necrosis factor (TNF). There is evidence to show that the addition of TNF and IL6 to HIV-infected T cells in vitro leads to increased multiplication of the virus. The TNF release associated with tuberculosis infection in an HIV-positive subject may precipitate proliferation of the HIV with consequential disruption of the function of T4 cells in the immune system and production of immunodeficiency.

It is believed that the prevention of tuberculosis or, more specifically, the inhibition of TNF, and IL6 associated (Koch) responses, will have a delaying effect on precipitation of the AIDS syndrome. The agents of the invention are believed to exert an immunomodulatory effect on pre-existent cell mediated necrotising responses, changing them to a non-nectrotising form of response and that this is due to decreased production of, or a change in function of, IL6 and TNF. It is also believed that protective immunity against both tuberculosis and leprosy are enhanced.

Among a group of patients being treated for tuberculosis were seventeen who were seropositive by the Wellcome ELISA for HIV1. All the patients were prescribed streptomycin, isoniazid, rifampicin and pyrazinamide for their tuberculosis. Therapy was abbreviated and did not last longer than three months in any case. Eight of the seventeen patients received the therapeutic agent of the present invention and nine received placebo (saline). At follow-up about one year later, only three of the patients who had received the anti-tuberculosis drugs only had survived and all three of these had advanced tuberculosis. Seven of the eight patients treated with the therapeutic agent of the present invention had become sputum smear negative for acid fast bacilli (i.e., tubercule bacilli) and the general improvement in their condition was similar to that in tuberculosis patients who were not HIV positive. Five of the eight patients had generalized lymphadenopathy at the time of diagnosis. This had resolved at the time of follow-up. The two patients who were re-tested serologically at the follow-up were found to be negative for HIV1.

It may be advantageous and is within the scope of the invention to use more than one strain of M. vaccae, and/or include in the therapeutic agent other mycobacterial antigens. Tuberculin may also be included.

The therapeutic agent may also contain BCG (Bacillus Calmette-Guerin) vaccine, in particular the freeze-dried form of the vaccine, to promote its effect.

The therapeutic agent can contain further ingredients such as adjuvants, preservatives, stabilizers, etc. It may be supplied in sterile injectable liquid form or in sterile freeze-dried form which is reconstituted prior to use.

*M. vaccae* may be used as such or as an extract or fractionated portion of the organism to prepare therapeutic agents according to the invention.

The following Example describes the preparation of a therapeutic agent as used in the invention.

EXAMPLE 1

Preparation of Therapeutic Agent

*M. vaccae* is grown on a solid medium comprising modified Sauton's medium solidified with 1.3% agar. The medium is inoculated with the microorganism and incubated for 10 days at 32° C. to enable growth of the microorganism to take place. The microorganisms are then harvested and weighed and suspended in diluent to give 100 mg of microorganisms/ml of diluent. The suspension is then further diluted with buffered saline to give a suspension containing 10 mg wet weight of microorganisms/ml of diluent and dispensed into 5 ml multidose vials. The vials containing the live microorganism are then autoclaved for 10 minutes at 10 psi to kill the microorganisms and give the immunotherapeutic agent of the invention, which may (if desired) be further diluted for use.

This immunotherapeutic agent may be administered by intradermal injection in the manner already described.

EXAMPLE 2

Stimulation of Immune Response in HIV Positive Subjects

A study was carried out to assess inter alia the effect of the administration of SRL 172, a vaccine comprising heat killed cells of *Mycobacterium vaccae* suspended in a buffered solution as described in Example 1, on the immune systems of HIV positive subjects who did not have tuberculosis.

25 subjects were enrolled in the trial, all of whom were being and continued to be treated with HAART (Highly active anti-retroviral therapy). Two months prior to the start of the trial, all subjects were tested for lymphocyte proliferation in response to challenge with various antigens. Each subject was classified as having a positive or negative response based on the lymphocyte proliferation in response to challenge with various antigens. Each subject was classified as having a positive or negative response based on the lymphocyte proliferation index to each of the challenges.

Amongst the antigens used as challenges were Candida (an antigen derived from *Candida albicans*), Tuberculin (derived from *Mycobacterium tuberculosis*, Malmoensin (derived from *Mycobacterium malmoense*), Ramin (derived from *Mycobacterium fortuilum*) and Gordonin (derived from *Mycobacterium gordonii*). These particular challenges are markers of the responses of the subjects' immune systems to the following respective infections:

a. candidiasis b. tuberculosis, and c. infection by three atypical mycobacteria (i.e. mycobacteria which produce symptoms distinct from those of tuberculosis)

These infections are all opportunistic infections recognized by the U.S. Centers for Disease Control as "AIDS-defining illnesses", and are familiar to those of skill in the art, along with other AIDS-defining illnesses as set forth in the criteria published by the Centers for Disease Control.

The subjects were then divided into two randomized groups to receive either SRL 172 (15 subjects) or placebo (10 subjects).

Each subject was injected on day 0, day 15 and day 30 of the trial with a 0.1 ml dose of either SRL 172 or placebo.

Following treatment, during the period from day 45 to day 90 of the trial, each subject was again tested for lymphocyte proliferation in response to challenges by the same antigens, and was again classified as having a positive or negative response.

The numbers of subjects showing positive or negative responses to the various challenges, both before and after treatment are tabulated in Table 1 (subjects receiving SRL 172) and Table 2 (subjects receiving placebo).

TABLE 1

15 HIV patients to whom *M. vaccae* administered

| Response | Before treatment | Negative | | Positive | | | |
|---|---|---|---|---|---|---|---|
| To Antigen | After treatment | Pos | Neg | Pos | Neg | | |
| | Column letter | A | B | C | D | E<br>[= A/(A + B)] | F<br>[= D/(C + D)] |
| Antigen | Candida | 1 | 0 | 13 | 1 | 100% | 7% |
| | Tuberculin | 4 | 3 | 8 | 0 | 57% | 0% |
| | Malmoensin | 4 | 2 | 8 | 1 | 67% | 11% |
| | Ramin | 6 | 0 | 7 | 2 | 100% | 22% |
| | Gordonin | 6 | 5 | 4 | 0 | 55% | 0% |

TABLE 2

10 HIV patients to whom a placebo was administered

| Response | Before treatment | Negative | | Positive | | | |
|---|---|---|---|---|---|---|---|
| To Antigen | After treatment | Pos | Neg | Pos | Neg | | |
| | Column letter | A | B | C | D | E<br>[= A/(A + B)] | F<br>[= D/(C + D)] |
| Antigen | Candida | 0 | 1 | 8 | 1 | 0% | |
| | Tuberculin | 0 | 3 | 4 | 3 | 0% | 43% |
| | Malmoensin | 2 | 4 | 3 | 1 | 33% | 25% |

TABLE 2-continued

10 HIV patients to whom a placebo was administered

| Ramin | 0 | 6 | 2 | 2 | 0% | 50% |
| Gordonin | 0 | 7 | 1 | 2 | 0% | 67% |

The numbers converting from negative to positive (indicating enhancement of the immune response) are shown in column E as a percentage of those starting the study with a negative response. The numbers converting from positive to negative (indicating compromise of the immune response) are shown in column F as a percentage of those starting the study with a positive response.

These results would indicate to a skilled medical practitioner, or other person of skill in the field of AIDS therapy, that the treatment with SRL 172 may by its action on the immune system delay or prevent the onset of, or reduce the subsequent severity of AIDS.

EXAMPLE 3

Reduction of Viral Load in HIV Positive Subjects

Twenty two HIV seropositive subjects were enrolled in the trial. Eleven of the subjects tested positive to tuberculin and had scars of prior BCG vaccination. There was not clinical evidence of tuberculosis disease in any of the twenty two. The skin test positivity to tuberculin indicated that eleven of the volunteers still had the capacity to produce an immunological response. None of the volunteers were suffering from or had ever suffered from tuberculosis. The subjects in this study were not receiving any other anti-HIV treatment. The following data relate to the eleven subjects who tested positive to tuberculin, indicating the capacity to produce an immunological response.

Each subject was given three doses of the inactivated *M. vaccae* vaccine at 0 months (dose 1), two months (dose 2) and four months (dose 3). The vaccine was given as an intradermal injection over the deltoid at a dosage level of 0.1 ml.

Plasma was collected from each subject at the start of the study (baseline) and two months after dose 3, and stored at −70° C. At the end of the trial, plasma samples from the subjects were shipped on dry ice to the USA, for quantification of HIV-1 viral load by bDNA assay (detection limit 500 copies/ml, Chiron Diagnostics, Emeryville, Calif).

When individuals were tested after the third injection of *M. vaccae*, it was found that there was a statistically significant reduction in viral load. The mean change in $\log_{10}$ viral load for tuberculin reactors was −0.49 (paired t-test= 4.83, p=0.0007), two months after the third dose of *M. vaccae*.

The results for each of the eleven patients studied are given in Table 3. These data relate to patients who were both HIV infected and tuberculin positive. These patients were injected with *M. vaccae* at 0 months, 2 months and 4 months, and tested for baseline viral load at month 0 and at 6 months (two months after the third injection).

TABLE 3

| | HIV viral load | |
| Patient No. | baseline | six months |
| --- | --- | --- |
| 702 | 45,150 | 7,469 |
| 703 | 2,913 | 1,851 |
| 718 | 10,200 | 5,429 |
| 724 | 136,900 | 34,990 |
| 726 | 70,600 | 25,110 |
| 728 | 38,140 | 10,960 |
| 730 | 26,860 | 4,029 |
| 731 | 11,700 | 8,307 |
| 732 | 11,700 | 2,427 |
| 747 | 21,810 | 29,140 |
| 750 | 121,100 | 12,860 |
| mean | 45,188 | 12,961 |
| median | 26,860 | 8,307 | p = 0.0007

These results would indicate to a skilled medical practitioner, or other person of skill in the field of AIDS therapy, that administration of *M. vaccae* to a subject infected with HIV is effective in reducing viral load of HIV and delaying or preventing the onset of, and/or reducing the subsequent severity of AIDS.

What is claimed is:

1. A method for reducing viral load in an HIV positive subject with or without AIDS, comprising administering to said subject killed cells of *Mycobacterium vaccae* in an amount effective to reduce HIV viral load in said patient.

2. A method according to claim 1, wherein the cells of *M. vaccae* have been killed by autoclaving.

3. A method according to claim 1, wherein the cells are of the strain deposited at the National Collection of Type Cultures (NCTC) Central Public Health Laboratory, Colindale Avenue, London NW9 5HT, United Kingdom on February 13th, 1984 under the number NCTC 11659.

4. A method according to claim 1, wherein the killed cells of *M. vaccae* are present in an amount comprising from $10^7$ to $10^{10}$ microorganisms per dose.

5. A method according to claim 1, wherein the subject suffers from tuberculosis.

6. A method of stimulating an immune response in an HIV positive subject with or without AIDS, comprising administering to said subject killed cells of *Mycobacterium vaccae* in an amount effective to stimulate an immune response in said subject.

7. The method according to claim 6 wherein the immune response is directed towards an organsim selected from the group consisting of *Candida albicans*, *Mycobacterium tuberculosis*, and atypical Mycobacteria.

8. The method according to claim 6 wherein the killed cells of *M. vaccae* are present in an amount comprising from $10^7$ to $10^{10}$ microorganisms per dose.

* * * * *

UNITED STATES PATENT AND TRADEMARK OFFICE
CERTIFICATE OF CORRECTION

PATENT NO.    : 6,432,714 B2
DATED         : August 13, 2002
INVENTOR(S)   : Stanford et al.

It is certified that error appears in the above-identified patent and that said Letters Patent is hereby corrected as shown below:

Title page,
Item [73], please add the following Related U.S. Application Data and Foreign Application Priority Data as follows:
-- [63]      Related U.S. Application Data
Continuation of PCT GB90/01169, filed on July 27, 1990.
    [30]     Foreign Application Priority Data
July 28, 1989    (GB) ............................................ 8917256
September 14, 1992    (GB) .............................. 9219425 --

Signed and Sealed this

Twentieth Day of May, 2003

JAMES E. ROGAN
*Director of the United States Patent and Trademark Office*